US00PP31881P2

(12) United States Plant Patent
Koot et al.

(10) Patent No.: US PP31,881 P2
(45) Date of Patent: Jun. 16, 2020

(54) **NEW GUINEA *IMPATIENS* PLANT NAMED 'DONGIMPETRESTA 19'**

(50) Latin Name: *Impatiens hawkeri*
Varietal Denomination: Dongimpetresta 19

(71) Applicant: DUMMEN GROUP B.V., De Lier (NL)

(72) Inventors: Arjan Koot, Oeffelt (NL); Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/501,415

(22) Filed: Apr. 9, 2019

(51) Int. Cl.
*A01H 5/02* (2018.01)
*A01H 6/16* (2018.01)

(52) U.S. Cl.
USPC ..... Plt./318.1

(58) Field of Classification Search
USPC ..... Plt./263.1, 317, 318.1
See application file for complete search history.

(56) References Cited

PUBLICATIONS

UPOV-PLUTO: Plant Variety Database, Sep. 12, 2019, citation for 'Dongimpetresta 19'. 1 page. (Year: 2019).*

Dummen Orange Bedding Plants 2015-2016 catalog. https://issuu.com/bepplersrl/docs/catalog_d_mmen_oragne_2015-2016. 2 pages (Year: 2016).*

* cited by examiner

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Impatiens* plant named 'Dongimpetresta 19' characterized by its upright to outwardly spreading and mounding plant habit; moderately vigorous growth habit; freely branching habit; dark green-colored leaves; freely and early flowering habit; medium to large bright red and light purplish pink bi-colored flowers; and good garden performance.

2 Drawing Sheets

Botanical designation: *Impatiens hawkeri.*
Cultivar denomination: 'DONGIMPETRESTA 19'.

BACKGROUND OF THE INVENTION

The present invention relates to a new and distinct cultivar of New Guinea *Impatiens* plant, botanically known as *Impatiens hawkeri* and hereinafter referred to by the name 'Dongimpetresta 19'.

The new *Impatiens* plant is a product of a planned breeding program conducted by the Inventors in Koka, Ethiopia and Rheinberg, Germany. The objective of the breeding program is to create new early and freely flowering New Guinea *Impatiens* plants with large attractive flowers and good garden performance.

The new *Impatiens* plant originated from a cross-pollination made by the Inventors in November, 2012 in Koka, Ethiopia of a proprietary selection of *Impatiens hawkeri* identified as code number NN10-001649-001, not patented, as the female, or seed, parent with a proprietary selection of *Impatiens hawkeri* identified as code number NN09-006631-004, not patented, as the male, or pollen, parent. The new *Impatiens* plant was discovered and selected by the Inventors as a single flowering plant from within the progeny of the stated cross-pollination in a controlled greenhouse environment in Rheinberg, Germany in April, 2013.

Asexual reproduction of the new *Impatiens* plant by terminal vegetative cuttings in a controlled greenhouse environment in Rheinberg, Germany since June, 2013 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Dongimpetresta 19'. These characteristics in combination distinguish 'Dongimpetresta 19' as a new and distinct *Impatiens* plant:

1. Upright to outwardly spreading and mounding plant habit.
2. Moderately vigorous growth habit.
3. Freely branching habit.
4. Dark green-colored leaves.
5. Freely and early flowering habit.
6. Medium to large bright red and light purplish pink bi-colored flowers.
7. Good garden performance.

Plants of the new *Impatiens* can be compared to plants of the female parent selection. Plants of the new *Impatiens* differ primarily from plants of the female parent selection in the following characteristics:

1. Plants of the new *Impatiens* are more vigorous than plants of the female parent selection.
2. Plants of the new *Impatiens* have larger flowers than plants of the female parent selection.
3. Flowers of plants of the new *Impatiens* are bright red and light purplish pink in color whereas flowers of plants of the female parent selection are dull red and light pink in color.

Plants of the new *Impatiens* can be compared to plants of the male parent selection. Plants of the new *Impatiens* differ primarily from plants of male parent selection in flower color as flowers of plants of the new *Impatiens* are bright red and light purplish pink in color whereas flowers of plants of the male parent selection are red and dark pink in color.

Plants of the new *Impatiens* can be compared to plants of *Impatiens hawkeri* 'Dueptbus 14', disclosed in U.S. Plant Pat. No. 26,780. In side-by-side comparisons, plants of the new *Impatiens* differ primarily from plants of 'Dueptbus14' in the following characteristics:

1. Plants of the new *Impatiens* are not as vigorous as plants of 'Dueptbus14'.
2. Plants of the new *Impatiens* have larger flowers than plants of 'Dueptbus14'.
3. Flowers of plants of the new *Impatiens* are bright red and light purplish pink in color whereas flowers of plants of 'Dueptbus14' are bright red and red purple in color.

Plants of the new *Impatiens* can be compared to plants of *Impatiens hawkeri* 'Duemagfi', disclosed in U.S. Plant Pat. No. 23,912. In side-by-side comparisons, plants of the new *Impatiens* differ primarily from plants of 'Duemagfi' in the following characteristics:

1. Lower leaf surfaces of plants of the new *Impatiens* are dark greyed purple in color whereas lower leaf surfaces of plants of 'Duemagfi' are dark green in color.
2. Plants of the new *Impatiens* flower later than plants of 'Duemagfi'.
3. Plants of the new *Impatiens* have smaller flowers than plants of 'Duemagfi'.
4. Flowers of plants of the new *Impatiens* are bright red and light purplish pink in color whereas flowers of plants of 'Duemagfi' are light red in color.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph on the first sheet is a side perspective view of a typical flowering plant of 'Dongimpetresta 19' grown in a container.

The photograph on the second sheet is a close-up view of a typical flowering plant of 'Dongimpetresta 19'.

DETAILED BOTANICAL DESCRIPTION

The aforementioned photographs and following observations, measurements and values describe plants grown during the winter and early spring in 15.25-cm containers in a polyethylene-covered greenhouse in Encinitas, Calif. and under cultural practices typical of commercial New Guinea *Impatiens* production. During the production of the plants, day temperatures averaged 25° C., night temperatures averaged 20° C. and light levels ranged from 4,000 to 4,500 lux. Plants were 16 weeks old when the photographs and description were taken. In the following description, color references are made to The Royal Horticultural Society Colour Chart, 2017 Edition, except where general terms of ordinary dictionary significance are used.

Botanical classification: *Impatiens hawkeri* 'Dongimpetresta 19'.

Parentage:

*Female, or seed, parent.*—Proprietary selection of *Impatiens hawkeri* identified as code number NN10-001649-001, not patented.

*Male, or pollen, parent.*—Proprietary selection of *Impatiens hawkeri* identified as code number NN09-006631-004, not patented.

Propagation:

*Type.*—By terminal vegetative cuttings.

*Time to initiate roots, summer and winter.*—About five to seven days at temperatures about 20° C.

*Time to produce a rooted young plant, summer and winter.*—About three to four weeks at temperatures about 20° C.

*Root description.*—Fine, fibrous; typically white in color, actual color of the roots is dependent on substrate composition, water quality, fertilizers, substrate temperature and age of roots.

*Rooting habit.*—Freely branching; dense.

Plant description:

*Plant and growth habit.*—Upright to outwardly spreading and mounding plant habit; broad inverted triangle in overall shape; freely branching habit with lateral branches potentially developing at every node; moderately vigorous growth habit and moderate growth rate.

*Plant height.*—About 36 cm.

*Plant diameter.*—About 55 cm.

Lateral branch description:

*Length.*—About 30.5 cm.

*Diameter.*—About 1.5 cm.

*Internode length.*—About 5.6 cm.

*Strength.*—Strong, stout.

*Aspect.*—Initially upright to outwardly spreading.

*Texture and luster.*—Smooth, glabrous; glossy.

*Color, developing.*—Close to 187A.

*Color, fully developed.*—Close to 187A to 187B.

Leaf description:

*Arrangement.*—Typically in whorls; simple.

*Length.*—About 11 cm.

*Width.*—About 4.7 cm.

*Shape.*—Lanceolate to elliptic.

*Apex.*—Acuminate.

*Base.*—Cuneate.

*Margin.*—Serrate with ciliation.

*Texture and luster, upper surface.*—Smooth, glabrous; glossy.

*Texture and luster, lower surface.*—Smooth, glabrous; somewhat glossy.

*Venation pattern.*—Pinnate; arcuate.

*Color.*—Developing and fully expanded leaves, upper surface: Darker green than N189A; venation, close to 187B. Developing and fully expanded leaves, lower surface: Close to 187B; venation, close to 187B.

*Petiole length.*—About 5.5 cm.

*Petiole diameter*.—About 4 mm.

*Petiole texture and luster, upper and lower surfaces*.—Smooth, glabrous; somewhat glossy.

*Petiole color, upper surface*.—Close to 187B to 187C.

*Petiole color, lower surface*.—Close to 187B.

Flower description:

*Flower type and flowering habit*.—Single oval to rounded axillary flowers that are undulate; freely flowering habit, typically about eight to ten open flowers and flower buds per lateral branch; flowers positioned above and beyond the foliar plane, flowers typically face mostly upright to outwardly.

*Flower longevity*.—Flowers typically last about four to seven days on the plant under greenhouse conditions; petals self-cleaning, gynoecium persistent.

*Fragrance*.—None detected.

*Natural flowering season*.—Year-round under greenhouse conditions; in the garden, flowering from spring until fall in California; early flowering habit, plants typically begin flowering about ten weeks after planting.

*Flower buds*.—Length: About 1.4 cm. Diameter: About 9 mm. Shape: Ovoid. Texture and luster: Smooth, glabrous; slightly glossy. Color: Petals, close to 53B; sepals, close to 187A to 187B.

*Flower diameter*.—About 5 cm by 5.5 cm.

*Flower depth*.—About 1 cm.

*Petals*.—Quantity and arrangement: Five per flower in a single whorl. Length, banner petal: About 2.3 cm. Length, lateral petals: About 2.4 cm. Length, lower petals: About 2.6 cm. Width, banner petal: About 3.8 cm. Width, lateral petals: About 2.5 cm. Width, lower petals: About 2.75 cm. Shape, banner petal: Broadly cordate. Shape, lateral and lower petals: Cordate. Apex, all petals: Cordate. Base, all petals: Cuneate. Margin, all petals: Mostly entire with occasional and random indentations. Texture and luster, all petals, upper surface: Smooth, glabrous; velvety; matte. Texture and luster, all petals, lower surface: Smooth, glabrous; matte. Color, all petals: When opening and fully opened, upper surface: Centers, close to between 45A and 46B; towards the margins, close to 55C; venation, similar to lamina; color does not change with development. When opening and fully opened, lower surface: Centers, close to between 45C and 46C; towards the margins, close to 55C; venation, similar to lamina; color does not change with development.

*Sepals*.—Quantity and arrangement: Three in a single whorl; one modified into an elongated spur. Lateral sepal length: About 1.1 cm. Lateral sepal width: About 6 mm. Lateral sepal shape: Elongated deltoid. Lateral sepal apex: Cuspidate. Lateral sepal base: Truncate. Lateral sepal margin: Entire. Lateral sepal texture and luster, upper surface: Smooth, glabrous; matte. Lateral sepal texture and luster, lower surface: Smooth, glabrous; slightly glossy. Lateral sepal color, upper surface: Close to 157B to 157C. Lateral sepal color, lower surface: Close to 178A. Spur length: About 4.75 cm. Spur diameter: At flower, about 2.5 mm; at apex, about 1 mm. Spur texture and luster: Smooth, glabrous; somewhat glossy. Spur color: Close to 54B; distally, close to 145A.

*Peduncles*.—Length: About 5 cm. Diameter: About 2 mm. Angle: About 30° to 45° from vertical. Strength: Strong; flexible. Texture and luster: Smooth, glabrous; slightly glossy. Color: Close to 146B.

*Reproductive organs*.—Stamens: Quantity: Five fused at anthers; filaments free. Anther size: About 5 mm by 1 mm. Anther shape: Oblong. Anther color: Close to 11D; proximally, close to N57A. Pollen amount: Moderate. Pollen color: Close to 10D. Pistils: Quantity per flower: One. Pistil length: About 5 mm. Stigma shape: Crested. Stigma color: Close to 144A. Style color: Close to 144A. Ovary color: Close to 144A.

*Seeds and fruits*.—To date, seed and fruit production has not been observed on plants of the new *Impatiens*.

Pathogen & pest resistance: To date, plants of the new *Impatiens* have not been observed to be resistant to pathogens and pests common to *Impatiens* plants.

Garden performance: Plants of the new *Impatiens* have been observed to have good garden performance and tolerate temperatures ranging from about 5° C. to about 40° C.

It is claimed:

1. A new and distinct *Impatiens* plant named 'Dongimpetresta 19' as illustrated and described.

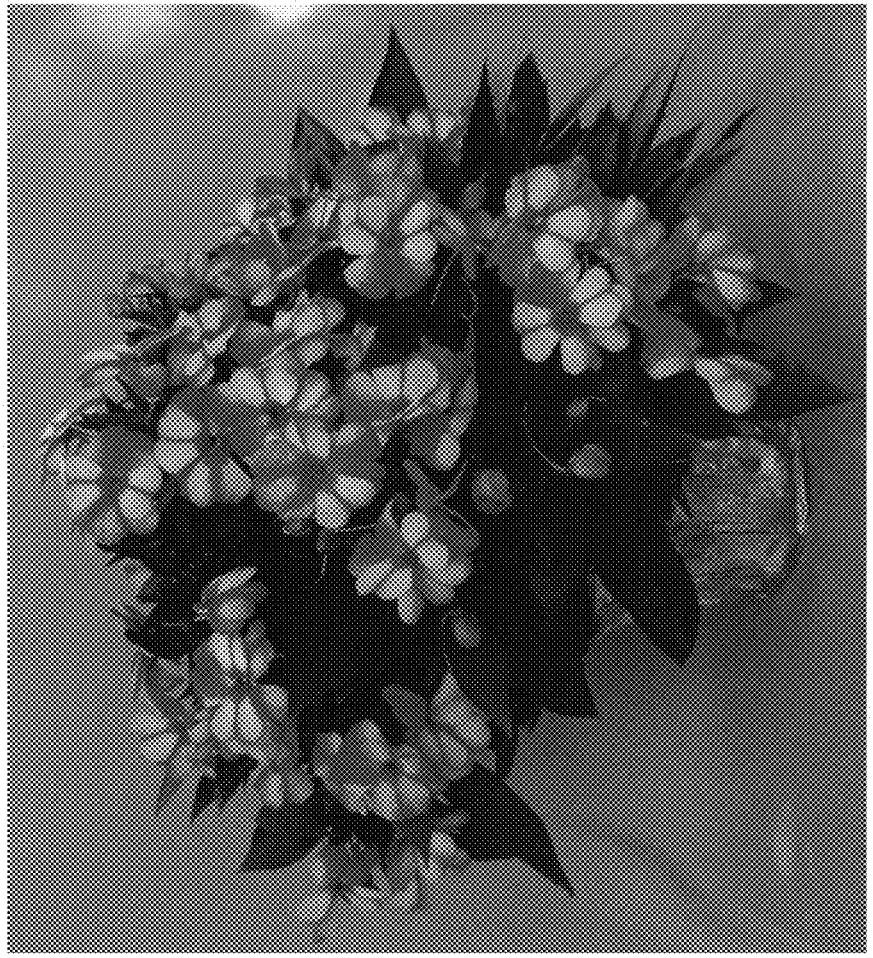

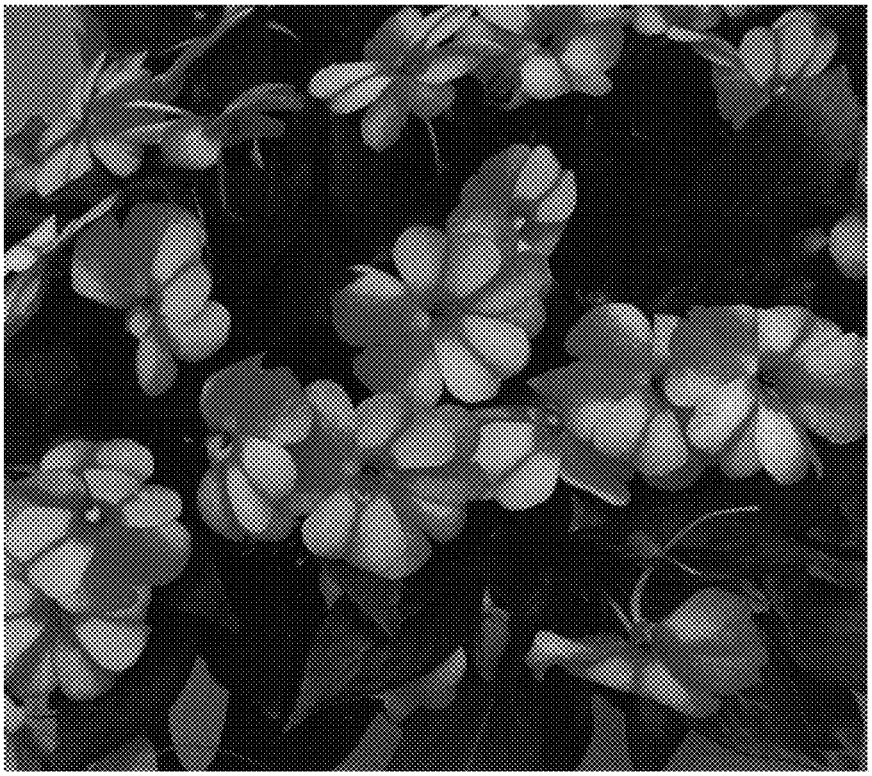

* * * * *